United States Patent [19]
Schultz

[11] Patent Number: 5,762,621
[45] Date of Patent: Jun. 9, 1998

[54] HAND TENDON SUPPORT SYSTEM

[76] Inventor: Anne Schultz, 5531 E. 23rd St., No. 10, Long Beach, Calif. 90815

[21] Appl. No.: 731,959

[22] Filed: Oct. 23, 1996

[51] Int. Cl.$^6$ .................................................. A61F 5/00
[52] U.S. Cl. ........................... 602/64; 602/60; 128/879; 128/880
[58] Field of Search ................... 602/20–21, 63, 602/64; 473/59, 61, 62; 2/161.1, 161.2–161.6, 162, 163, 21, 161.7; 128/878–880

[56] References Cited

U.S. PATENT DOCUMENTS

| | | | |
|---|---|---|---|
| 1,863,960 | 6/1932 | Aronson | 473/61 |
| 3,164,841 | 1/1965 | Burtoff | 2/21 |
| 3,298,366 | 1/1967 | Moore et al. | 128/169 |
| 4,047,250 | 9/1977 | Norman | 2/161.1 |
| 4,183,100 | 1/1980 | De Marco | 2/161.3 X |
| 4,716,892 | 1/1988 | Brunswick | 602/21 |
| 5,033,119 | 7/1991 | Wiggins | 2/161.3 X |
| 5,295,269 | 3/1994 | Ballard | 2/161.1 X |
| 5,376,066 | 12/1994 | Phillips | 602/21 |
| 5,413,553 | 5/1995 | Downes | 602/21 |
| 5,498,234 | 3/1996 | Martel | 602/21 X |
| 5,513,657 | 5/1996 | Nelson | 602/21 X |
| 5,538,501 | 7/1996 | Caswell | 602/21 X |

OTHER PUBLICATIONS

*The Reporter*, Tuesday, Jan. 7, 1997, vol. 76, No. 3 p. 8.

Primary Examiner—Richard J. Apley
Assistant Examiner—Denise Pothier
Attorney, Agent, or Firm—Curtis L. Harrington

[57] ABSTRACT

The glove and associated structures provide both healing and support pressure on the user's tendons. When properly used, the integrated glove and associated structures will significantly aid in the support and healing of the hands, wrists and fingers of users. Not only will passive use of the tendon support structures help heal and soothe damaged tendons, but they will also help the user perform work tasks. In a first embodiment, an integrated glove provides finger and upper wrist support portion, along with a lower wrist band attached to the upper wrist support portion. In a second embodiment, a band system includes finger bands, a palm band, an upper wrist band and a lower wrist band which is used without interconnecting fabric, and the components of which may be used independently as needed. A third embodiment has a wrist band having palm band and wrist band portions. In this manner, the system provides not only passive healing, but also active support to prevent further harm to the tendons of the fingers, wrist and hands under working conditions.

8 Claims, 5 Drawing Sheets 5,762,621

HAND TENDON SUPPORT SYSTEM

FIELD OF THE INVENTION

The present invention relates to theraputic and protective structures worn on the hand, wrist and forearm, and more specifically to a supportive elastic glove and portions thereof for wrist and hand support.

BACKGROUND OF THE INVENTION

Individuals, even those whose hands, wrists and arms are otherwise healthy can experience severe hand, finger and wrist pain when strenuous and difficult work is performed. Those who are involved with assembly line work, or other work requring awkward hand positioning, and in particular awkward hand positioning coupled with significant manipulative force often suffer extreme pain and loss of manipulative control. Aside from the pain and loss of control, the damage to the tendons and surrounding tissue can be significant. Further, where the worker depends upon the ability to use his hands, strained tendons can result in lost work time and medical expenses.

The main remedy for strained tendons is rest and possibly a topical preparation for warming the wrist and hand and increasing the blood flow. Another remedy is the use of a wrap to isolate the hand and wrist, such as a stretch bandage for immobilizing the problem areas. This is not much help where the objective is to continue work as the tendons heal.

SUMMARY OF THE INVENTION

The glove and associated system structures of the present invention provide both healing and support pressure on the user's tendons. When properly used, the integrated glove and associated system structures will significantly aid in the support and healing of the hands, wrists and fingers of users. Not only will passive use of the tendon support structures help heal and soothe damaged tendons, but they will also help the user perform work tasks. In a first embodiment, an integrated glove provides finger and upper wrist support portion, along with a lower wrist band attached to the upper wrist support portion. In a second embodiment, a band system includes finger bands, a palm band, an upper wrist band and a lower wrist band which is used without interconnecting fabric, and the components of which may be used independently as needed. In this manner, the system provides not only passive healing, but also active support to prevent further harm to the tendons of the fingers, wrist and hands under working conditions.

BRIEF DESCRIPTION OF THE DRAWINGS

The invention, its configuration, construction, and operation will be best further described in the following detailed description, taken in conjunction with the accompanying drawings in which.

DETAILED DESCRIPTION OF THE PREFERRED EMBODIMENT

Figure 1:
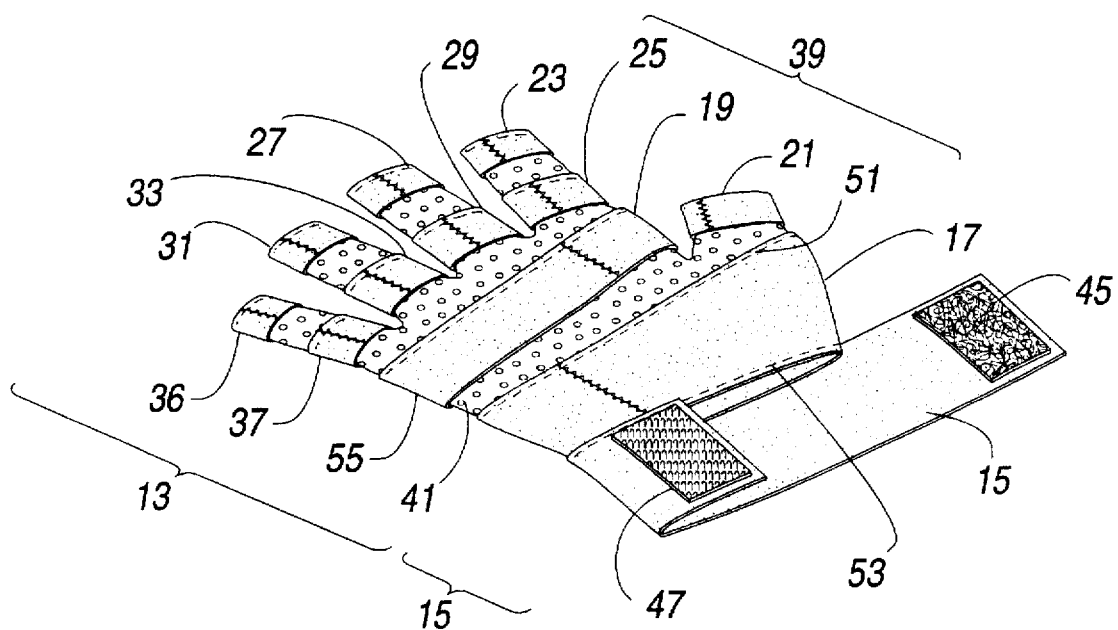
FIG. 1 is a perspective view of a first embodiment of the present invention including an integrated glove with finger, palm, wrist and lower wrist portions joined into an integrated structure.

The description and operation of the invention will be best described with reference to FIG. 1. FIG. 1 illustrates an integrated glove 11 having a series of attached portions to be described. Integrated glove 11 provides support and stops pain while allowing flexability of the hand, wrist, and fingers. The glove provides warmth, massage of tissues for the wearer thereof, yet allows the wearer to function manually. The integrated glove 11 supports and protects bones, tendons, nerves and ligaments during repetitive use of the wrists, hands and fingers.

In general, the integrated glove 11 of FIG. 1 includes a glove portion 13 and lower wrist strap portion 15 joined to the glove portion 13 at one or more points. The fewer the number of joinder points, the more flexibility which can be employed in fitting the lower wrist strap portion 15, and the more flexibility which can be had for the wearer. The greater flexibility will result from independent movement of the glove portion 13 with respect to the lower wrist band portion 15.

Referring to glove portion 13, it has an upper wrist band portion 17, a palm band portion 19 and finger band portions. The finger band portions include a thumb band portion 21, an upper first finger band portion 23, a lower first finger band portion 25, an upper second finger band portion 27, a lower second finger band portion 29, an upper third finger band portion 31, a lower third finger band portion 33, an upper fourth finger band portion 35, and a lower fourth finger band portion 37. The band portions 17, 19, 21, 23, 25, 27, 29, 31, 33, 35, & 37, will be collectively referred to as band portions 39.

All of the band portions 39, as well as the lower wrist band portion 15 may be preferably made from a stretchable material which has good stretch-force characteristics.

All of the glove portions 13 structures are attached to a stretchable mesh fabric portion 41. The stretchability of fabric portion 41 will enable the band portions 39 to be adjustably positioned on the user's hand to the most comfortable position. The give and take of the fabric portion 41 will enable such manipulation. Also shown in FIG. 1 is an area of hook members 45 and an area of loop members 47 which enable the lower wrist band portions 15 to be adjusted to give the proper tension. As such, the lower wrist band portion 15 is made from a single length of material and has no other seams.

The upper wrist band portion 17 is attached to the outside of the fabric portion 41 by a pair of stitches, namely an upper stitch 51 and a lower stitch 53. As is shown, the upper wrist band portion 17 is sized to cover the thumb lower knuckle. Palm band portion 19 has only an upper stitch 55. Other than the upper wrist band portion 17, all of the other band portions 39 carry only an upper, singular circular stitch such as upper stitch 55 of palm band portion 19. This enables the user to reach behind the band portions 39 having only one stitch to readjust the band portions 39 on the integrated glove 11 for an optimum fit. The single stitches for all of the other band portions 39, not including wrist band portion 17 are not shown in FIG. 1 for convenience.

Figure 2:
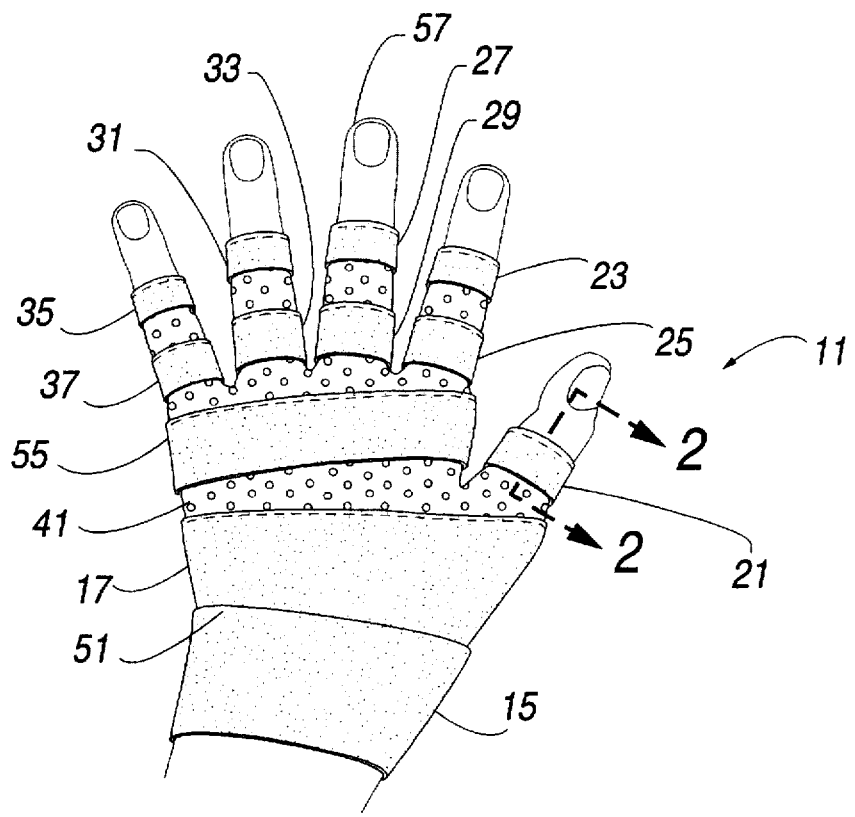
FIG. 2 is a plan view of the integrated glove of FIG. 1 shown on a wearer's hand.

Referring to FIG. 2, a users's hand 57 is shown to illustrate the integrated glove 11 and from a view at the back side of the hand. The expansion to fit nature of the integrated glove 11 is now more fully seen. The upper band portion 17 is seen covering the lower thumb knuckle.

Figure 3:
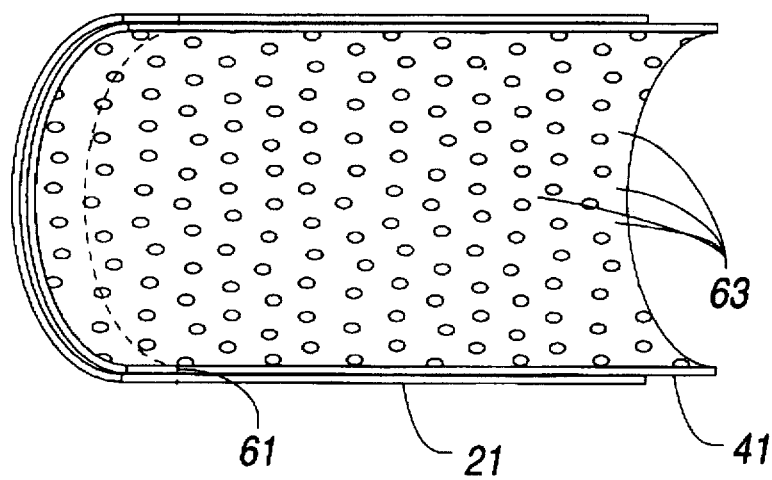
FIG. 3 is a sectional view taken along line 2—2 of FIG. 2 and illustrating the sewn construction of one of the digit openings in the integrated glove of FIGS. 1 & 2, namely the thumb.

Referring to FIG. 3, a view taken along line 2—2 of FIG. 2 illustrates the construction of both the mesh fabric 41 and thumb band portion 21. The thumb band portion 21 has a single circular stitch 61 which joins it to the mesh fabric portion 41 in the area of the thumb band portion 21 of the glove 11. From the perspective of the viewer, the tip of the thumb band portion 21 is to the left of FIG. 3.

Note also the open spaces 63 which are shown in one version of the mesh fabric 41. These open spaces 63 help the user have additional ventilation. In mesh fabric 41, voids 63 can occur in a variety of sizes and in some cases are so large that they dominate the area of the mesh fabric portion 41.

Figure 4:
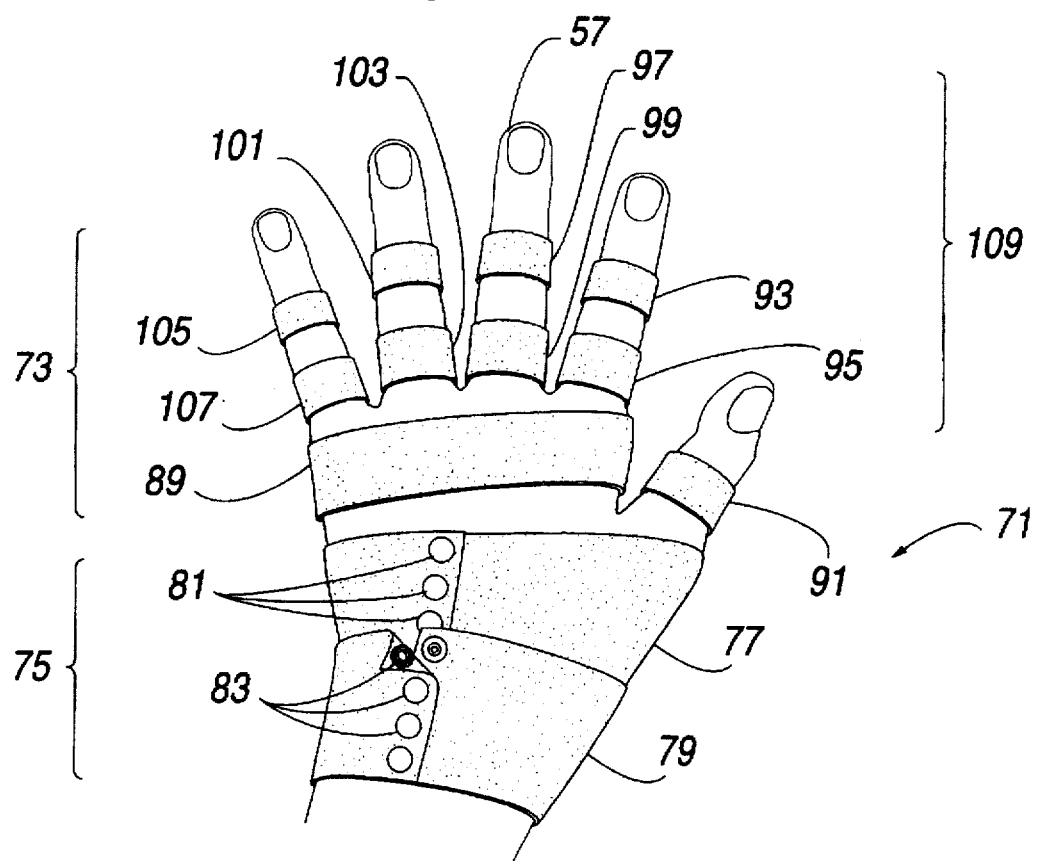
FIG. 4 is a second embodiment of the invention as a pressure system and shown on the hand of a user and including individual pressure bands for the fingers, palm, wrist and lower wrist.

Referring to FIG. 4, a second embodiment is shown on hand 57. In the second embodiment, the bands 39 of the first embodiment are provided in the form of a band system 71, and are not portions of an integrated glove. The band system 71 will ideally be available as a set or kit which will enable the user to pick and choose the protection which is needed. For example, where only the fingers are desired to be supported, the system 71 enables selective support of only the fingers. Where only the wrist is desired to be supported, the system 71 enables varying degrees of support for the wrist also.

In general, the integrated system of FIG. 4 includes a finger and palm system 73 and lower wrist system 75. The separate nature of the system provides even more flexibility than the integrated glove 11.

Referring to the lower wrist system 75, it has an upper wrist band 77, and a lower wrist band 79. The upper wrist band 77 is primarily to prevent carpel tunnel syndrome, and covers the lower knuckle of the thumb. The upper wrist band 77 has a series of snaps 81 which enable its ends to be joined together. Note that the upper wrist band 77 forms an obtuse angle at the upper end of the series of snaps 81. The lower wrist band 79 also has a series of snaps 83 and is partially covering upper wrist band 77 and its snaps 81. The length of the wrist bands 77 and 79 may vary, and several sized lengths of this band may be included in a kit to be shown. By providing multiple bands in the lower band system 75, they may be adjusted and overlapped and even doubled to provide extra pressure where needed.

The finger and palm system 73 includes a palm band 89 and finger bands, including a thumb band 91, an upper first finger band 93, a lower first finger band 95, an upper second finger band 97, a lower second finger band 99, an upper third finger band 101, a lower third finger band 103, an upper fourth finger band 105, and a lower fourth finger band 107. The bands 89, 91, 93, 95, 97, 99, 101, 103, 105, 107, will be collectively referred to as bands 109.

All of the bands 109, as well as the band portions 39 may be made from a stretchable material which has good stretch-force characteristics. Preferable materials include neoprene and other materials having a good quality finish, and which will have desired stretch characteristics. The stretch characteristics will include a relationship of force exerted per unit of stretch. Larger sizes may be more stretchy that smaller sizes to insure that a sufficient amount of stretch is applied to the wrist and hands. As for the mesh portion, or the glove fabric portion 41, a nylon jersey mesh is preferable.

Figure 5:
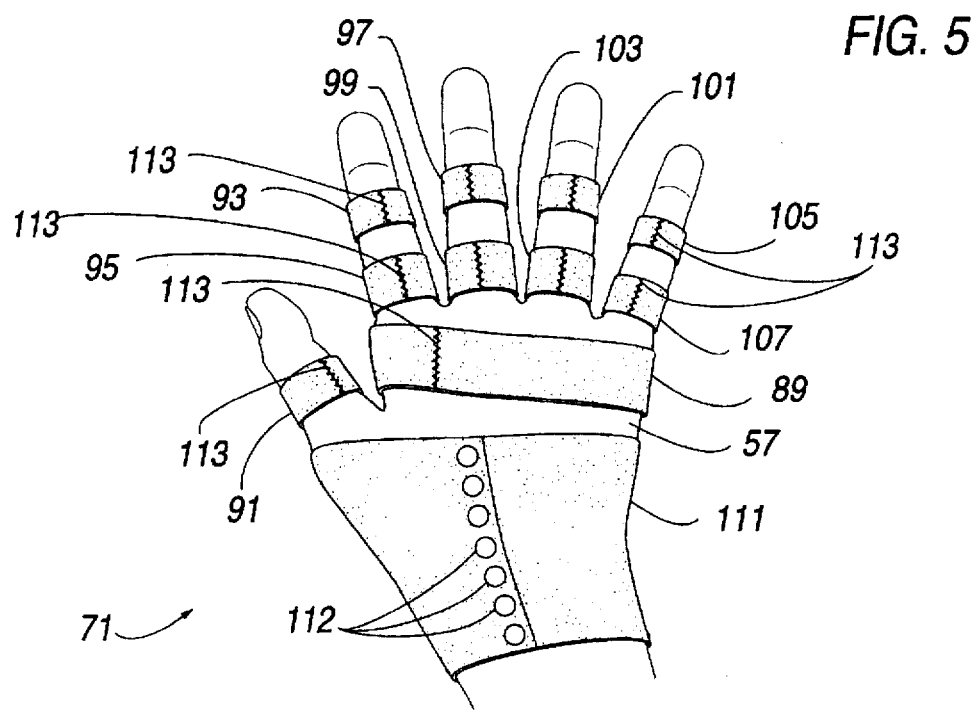
FIG. 5 is a view of the reverse side of the pressure system of FIG. 4 and illustrating the joinder seams for the bands; and, FIG. 6 is a kit, including the pressure system of FIGS. 4 & 5 including a washable bag for storage of the system, as well as for enabling the system to be washed along with the bag to prevent any portion of the system from being misplaced.

Referring to FIG. 5, a users's hand 57 is shown to illustrate the bands 109 and a single piece wrist band 111. The single piece wrist band 111 replaces the multiple wrist bands shown in FIG. 4, and has a series of snaps 112.

Either the single piece wrist band 111 or the combination of the upper wrist band 77, and a lower wrist band 79 may be used in conjunction with the other structures shown in FIG. 5, based upon the preferences and needs of the wearer. In some cases a sufficient number of wrist bands may be included in a deluxe kit which enables the wearer to pick and choose the wrist bands 77, 79 or 111 which are to be worn. Each of the bands 109 has a seam 113, some of which are shown as numbered as spacing allows.

Figure 6:
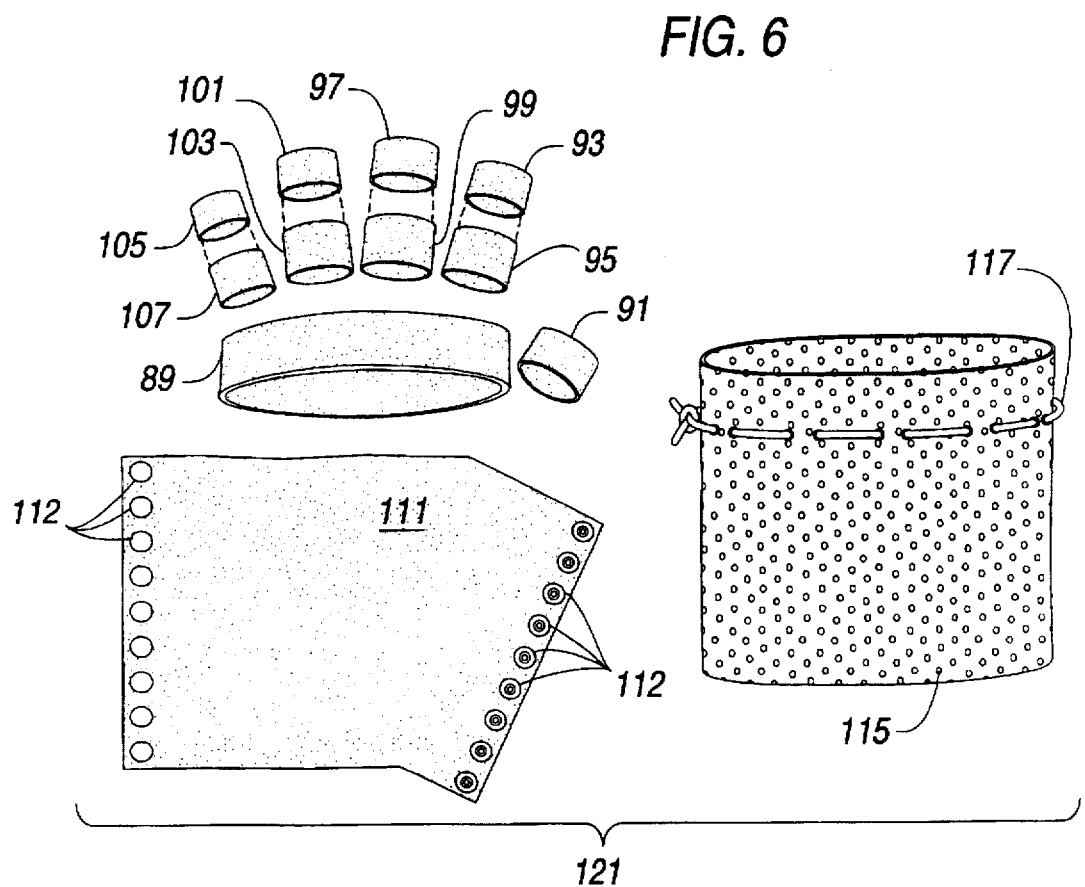

Referring to FIG. 6, the bands 109 as well as the one piece wrist band 111, are shown in a position removed from the hand 57. As can be seen in a flattened view, the single piece wrist band 111 has a greater portion which is in the shape of a square band, and a lesser portion which is also in the shape of a square band, but which meets the greater portion at is an angle. This angulation facilitates the coverage of the single piece wrist band 11 over the lower knuckle of the thumb.

In addition, a mesh nylon washing bag 115 having a draw string 117 is illustrated. The system 71 may then be provided as a kit 121 which includes the system 71 and washing bag 115 with drawstring 117. The kit 121 may also include the upper and lower bands 77 and 79, again based upon the preferences and needs of the wearer.

The system 71 can be made of different sizes for different sized hands 57. The fabric portion can be made to any standard glove size. As an example for an extra small hand 57 size the system 71 will have the following dimensions. The lower wrist strap 79 has a nominal width of 2.25 inches and a length around the wrist of 6.75 inches and uses three snaps 83. The upper wrist band 77 will have a width of about 3.0 inches, a length of its upper edge of about 8.37 inches and a length of its lower edge of about 6.125 inches. The palm band 89 has a width of ⅞ of an inch an a length of about 6.75 inches.

The finger bands, for the extra small size has the following dimensions. Thumb band 91 has a width of about ⅝ of an inch and a length of about 2.25 inches. The upper first finger band 93 has a width of about ⅝ of an inch and a length of about 1.75 inches. The lower first finger band 95 has a width of about⅝ of an inch and a length of about 2.25 inches. The upper second finger band 97 has a width of about⅝ of an inch and a length of about 1.75 inches. The lower second finger band 99 has a width of about ⅝ of an inch and a length of about 2.25 inches. The upper third finger band 101 has a width of about ⅝ of an inch and a length of about 1.75 inches. The lower third finger band 103 has a width of about ⅝ of an inch and a length of about 2.25 inches. The upper fourth finger band 105 has a width of about ½ of an inch and a length of about 1.5 inches. The lower fourth finger band 107 has a width of about⅝ of an inch and a length of about 2.0 inches.

The same and associated dimensions would apply to the integrated glove 11, glove portion 13, lower wrist strap portion 15, and band portions 39. The starting dimensions will also depend upon the stretch/force characteristics of the materials used. Again, the preferred material is believed to be neoprene or similar material. However, layers of material, including stretch nylon laid over other fabrics, for example could work equally as well. Very stretchy material for the bands will dictate smaller length or diameter starting sizes, whereas less stretchy material will have a starting dimension which is larger and which will be equal to the final dimensions.

Figure 7:
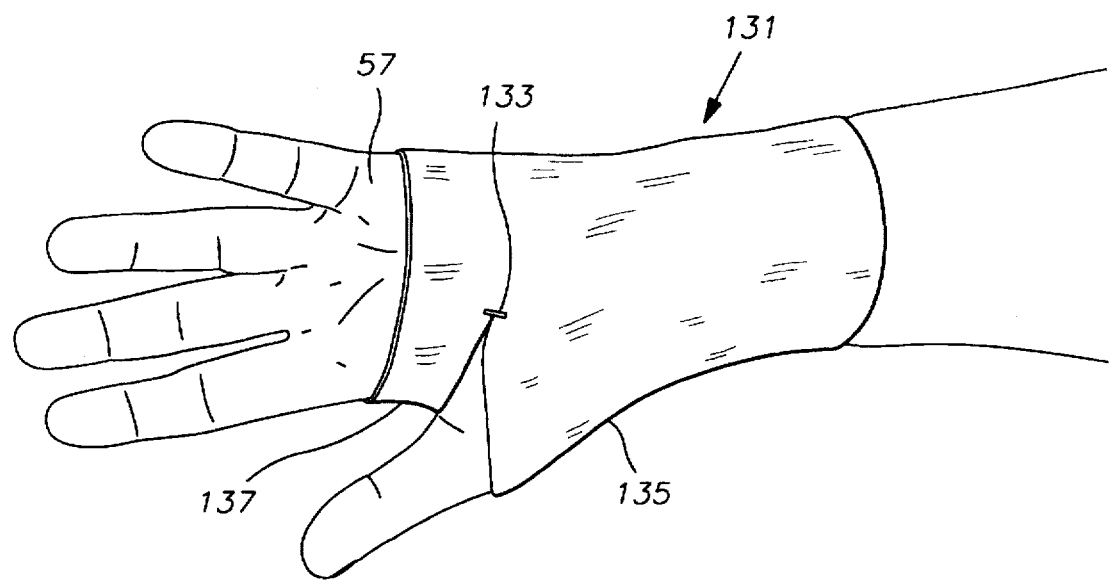
FIG. 7 illustrates the palm side of a one piece wrist and palm band support.
Figure 8:
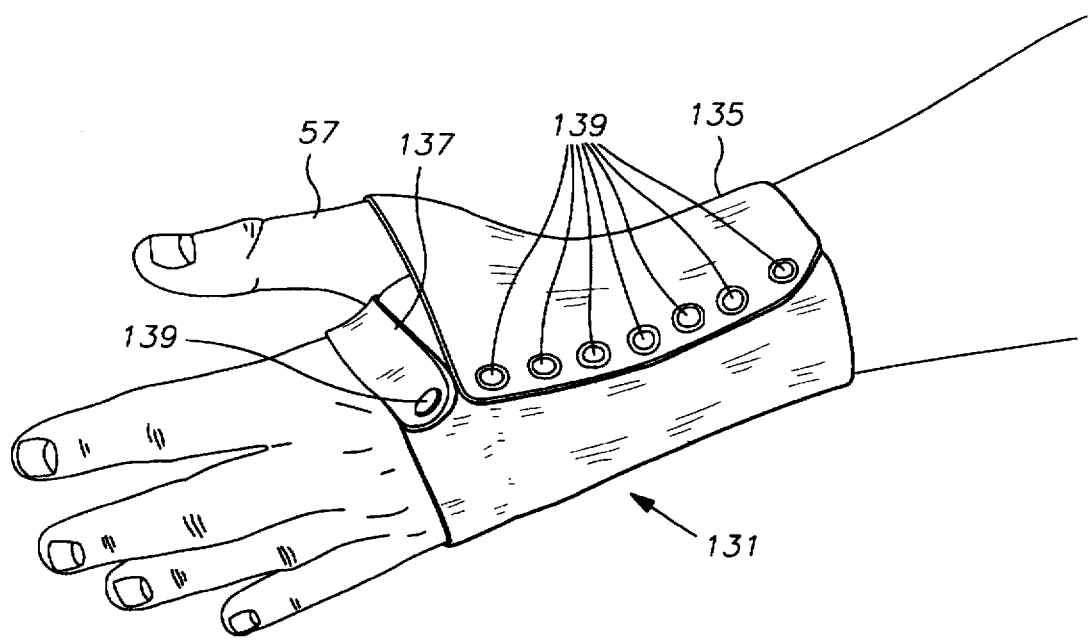
FIG. 8 illustrates the rear of the one piece wrist and palm band support of FIG. 7.

Referring to FIG. 7 a one piece wrist and palm band support 131 is shown, and which is pictured as covering the lower thumb knuckle. A single reinforcing stitch 133 is shown which is used to prevent tearing and separation where the side end of the support 131 splits into a wrist-thumb strap portion 135 and a palm strap portion 137. Referring to FIG. 8, the snaps 139 are seen.

Figure 9:
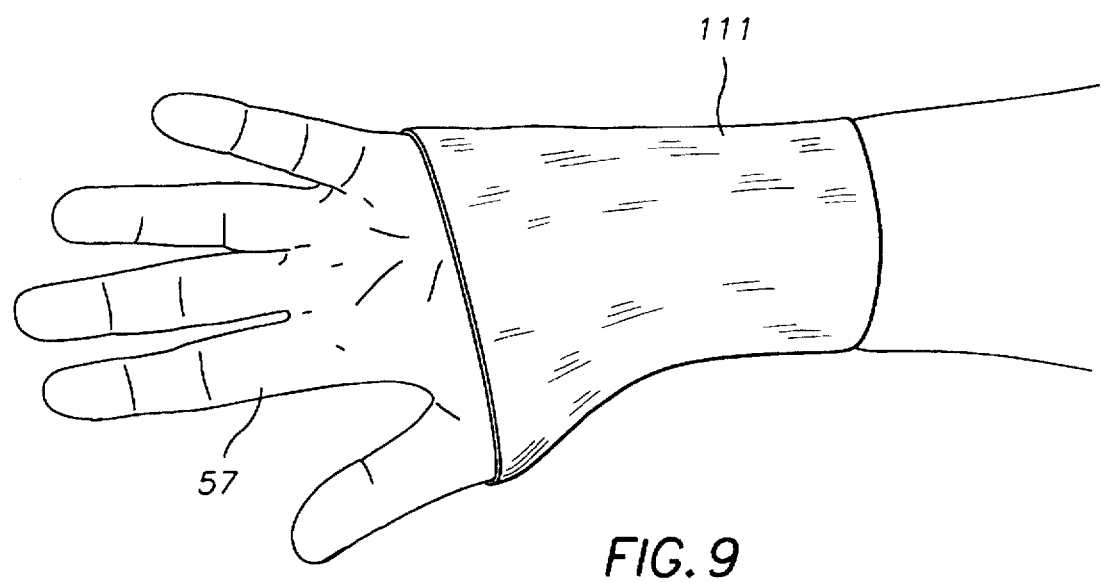
FIG. 9 illustrates the palm side of a one piece wrist strap support.
Figure 10:
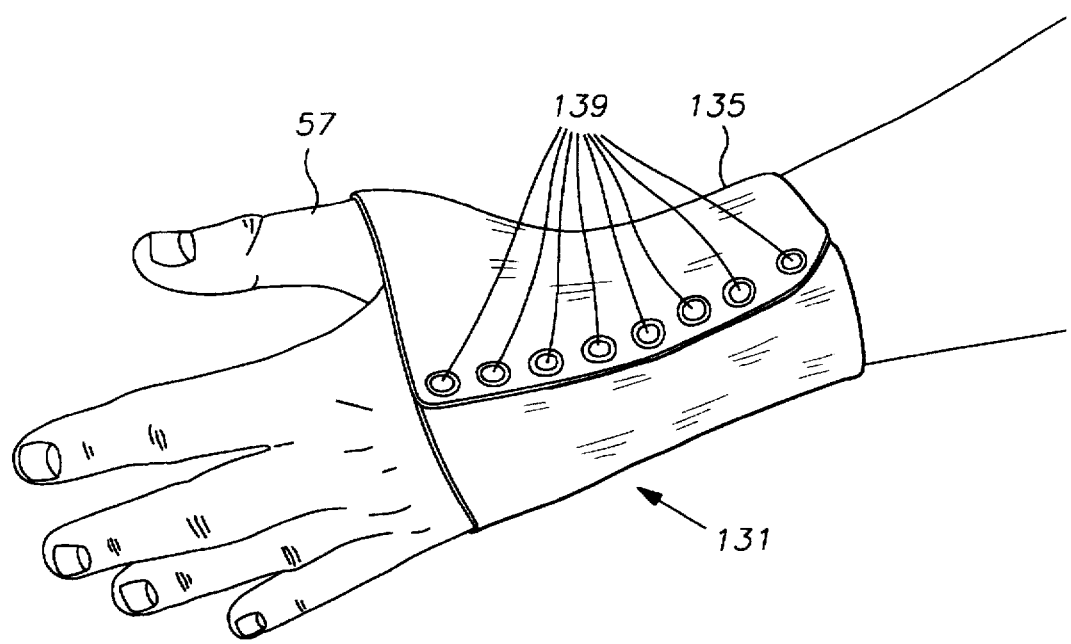
FIG. 10 illustrates the rear of the one piece wrist strap support of FIG. 9.

Referring to FIG. 9, the one piece strap 111 is shown in place with respect to a human hand 57. Note that the more widely flared end of the strap 111 should ideally go partially over the thumb to support the thumb. FIG. 10 illustrates the othe side of the one piece strap 111 as it stands alone, and is shown with snaps 139.

While the present invention has been described in terms of structures for supporting the fingers, hands and wrists in both a passive healing and in an active working environment, one skilled in the art will realize that the structure and techniques of the present invention can be applied to many similar devices. The present invention may be applied in any situation where flexible hand and wrist and finger support is to be had without limiting movement of the fingers, hands, and wrist.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. An integrated glove for the support of the fingers, hand and wrist, comprising:
   a fabric portion for fitting over a human hand, to partially cover the digits of a human hand and enable ends of the digits of the human hand to protrude therethrough;
   an upper wrist band portion attached to said fabric portion; and
   a plurality of reinforcing finger band portions attached to overlie and surround said fabric portion and to put additional circumferential pressure on the digits of the human hand through said fabric portion and surrounding the portions of said fabric portion where the ends of digits of the human hand are to protrude therethrough;
   a lower wrist band portion attached to said upper wrist band portion in an overlapping relationship and which lies partially over said upper wrist band portion at a length of attachment of said lower wrist band portion, such that an upper portion of said lower wrist band portion adds compression both to a part of said upper wrist band portion and said fabric portion, and wherein said lower wrist band portion has a first end and a second end and a middle part, said middle part attached to said upper wrist band portion and further including one of an area of hook and loop members attached to said first end of said lower wrist band portion, and the other of said hook and loop members attached to said second end of said lower wrist band portion.

2. The integrated glove for support of the fingers, hand and wrist as recited in claim 1 wherein each of said plurality of finger band portions is attached to said fabric portion by a single line of stitching.

3. The integrated glove for support of the fingers, hand and wrist as recited in claim 2 wherein each of said plurality of finger band portions has an upper edge and a lower edge and wherein said single line of stitching is located adjacent said upper edge of and completely surrounding each finger band portion.

4. The integrated glove for support of the fingers, hand and wrist as recited in claim 2 wherein said plurality of finger band portions further includes:
   a thumb band portion attached to said fabric portion;
   a first finger band portion attached to said fabric portion;
   a second finger band portion attached to said fabric portion;
   a third finger band portion attached to said fabric portion; and
   a fourth finger band portion attached to said fabric portion.

5. The integrated glove for support of the fingers, hand and wrist as recited in claim 4 and further comprising a palm band portion attached to overlie and surround said fabric portion, and attached to said fabric portion about a circumference of said fabric portion and to put additional circumferential pressure on the digits of the human hand through said fabric portion.

6. The integrated glove for support of the fingers, hand and wrist as recited in claim 5 wherein said palm band portion is attached to said fabric portion by a single line of stitching.

7. The integrated glove for support of the fingers, hand and wrist as recited in claim 6 wherein said palm band portion has an upper edge and a lower edge and wherein said single line of stitching is located adjacent said upper edge of said palm band portion.

8. A support system comprising:
   a carpel tunnel upper wrist compression band having an upper edge, a lower edge shorter than said upper edge, a first end having one of a male and female series of snaps and a second end having the other of a male and female series of snaps, the male snaps joinable to said female snaps to form said carpel tunnel compression band, the distance between said upper edge and said lower edge sufficient to cover the lower thumb knuckle joint of the human hand;
   a lower wrist compression band having a first end having one of a male and female series of snaps and a second end having the other of a male and female series of snaps, the male snaps joinable to said female snaps to form said lower wrist compression band and wherein said lower wrist compression band is fittable partially over said carpel tunnel upper wrist compression band;
   a plurality of unattached finger bands and an unattached thumb band for being worn over the fingers and thumb respectively, in conjunction with the wearing of said carpel tunnel upper wrist compression band and said lower wrist compression band; and
   an unattached palm band for wearing across the palm of a hand in conjunction with the wearing of said carpel tunnel upper wrist compression band and said lower wrist compression band, said plurality of finger bands and said thumb band.

* * * * *